United States Patent
Bartsch et al.

(10) Patent No.: US 7,671,229 B2
(45) Date of Patent: Mar. 2, 2010

(54) METHOD FOR THE PRODUCTION OF PENTENE NITRILES FROM N-BUTANE

(75) Inventors: Michael Bartsch, Neustadt (DE);
Robert Baumann, Mannheim (DE);
Gerd Haderlein, Grünstadt (DE);
Götz-Peter Schindler, Mannheim (DE);
Tim Jungkamp, Kapellen (BE);
Hermann Luyken, Ludwigshafen (DE);
Jens Scheidel, Hirschberg (DE);
Andreas Brodhagen, Bierbeeg (BE)

(73) Assignee: BASF SE, Ludwigshafen (DE)

( * ) Notice: Subject to any disclaimer, the term of this patent is extended or adjusted under 35 U.S.C. 154(b) by 582 days.

(21) Appl. No.: 10/586,451

(22) PCT Filed: Jan. 27, 2005

(86) PCT No.: PCT/EP2005/000773

§ 371 (c)(1),
(2), (4) Date: Jul. 18, 2006

(87) PCT Pub. No.: WO2005/073166

PCT Pub. Date: Aug. 11, 2005

(65) Prior Publication Data

US 2008/0275266 A1      Nov. 6, 2008

(30) Foreign Application Priority Data

Jan. 29, 2004   (DE) ..................... 10 2004 004 697

(51) Int. Cl.
*C07C 253/10* (2006.01)
(52) U.S. Cl. .................................................... 558/338
(58) Field of Classification Search .................. 558/338
See application file for complete search history.

(56) References Cited

U.S. PATENT DOCUMENTS

| | | | |
|---|---|---|---|
| 4,504,692 | A * | 3/1985 | Arakawa et al. ............ 585/633 |
| 6,169,198 | B1 | 1/2001 | Fischer et al. |
| 6,197,992 | B1 | 3/2001 | Fischer et al. |
| 6,242,633 | B1 * | 6/2001 | Fischer et al. ................ 558/334 |

FOREIGN PATENT DOCUMENTS

| | | | |
|---|---|---|---|
| DE | 19652273 | A1 | 6/1998 |
| GB | 628686 | * | 3/1950 |
| WO | WO-99/07671 | | 2/1999 |

OTHER PUBLICATIONS

Weissermahl, Arpe; Industrielle Organische Chemie; p. 119-121; Wiley-VCH; 1998.

* cited by examiner

*Primary Examiner*—Joseph R Kosack
(74) *Attorney, Agent, or Firm*—Connolly Bove Lodge & Hutz LLP

(57) ABSTRACT

A process is described for hydrocyanating 1,3-butadiene over at least one nickel(0) complex having phosphorus ligands as a catalyst, wherein the 1,3-butadiene is used in a mixture with n-butane and the mixture contains from 60 to 90% by volume of 1,3-butadiene and from 40 to 10% by volume of n-butane.

5 Claims, No Drawings

METHOD FOR THE PRODUCTION OF PENTENE NITRILES FROM N-BUTANE

CROSS REFERENCE TO RELATED APPLICATIONS

This application is a National Phase of PCT/EP2005/000773, filed Jan. 27, 2005, which claims priority to German application no. 102004004697.2 filed Jan. 29, 2004.

The present invention relates to a process for hydrocyanating 1,3-butadiene over at least one nickel(0) complex having phosphorus ligands as a catalyst.

Adiponitrile is an important starting material in nylon production, which is obtained by double hydrocyanation of 1,3-butadiene. In a first hydrocyanation, 1,3-butadiene is hydrocyanated to 3-pentenenitrile. In a second, subsequent hydrocyanation, 3-pentenenitrile is reacted with hydrogen cyanide to give adiponitrile. Both hydrocyanations are catalyzed by nickel(0) complexes having phosphorus ligands.

For the practice of this process for preparing adiponitrile, the costs and the origin of the feedstocks utilized are of crucial importance, since they generally make up 70% of the production costs.

In the adiponitrile synthesis from 1,3-butadiene and hydrogen cyanide, the use of pure 1,3-butadiene in the hydrocyanation reaction is disadvantageous, since 1,3-butadiene is customarily removed from the $C_4$ cut of steamcrackers by a complicated extraction; see, for example, Weissermehl, Arpe; Industrielle Organische Chemie; page 119 ff.; Wiley-VCH 1998.

To save extraction costs, DE 196 52 273 states that a crude $C_4$ cracker cut can be used in the hydrocyanation instead of pure 1,3-butadiene. This $C_4$ cracker cut contains generally 40% 1,3-butadiene, 5% alkynes and allenes, and 55% mono- and polyolefins. While the olefins behave substantially inertly in the hydrocyanation, the alkynes and allenes have to be removed from the mixture before the hydrocyanation, for example by an additional partial hydrogenation, since there is otherwise formation of undesired by-products and inhibition of the catalyst. Owing to the high proportion of about 60% of inert components, the space-time yield when these partially hydrogenated $C_4$ cracker cuts are used is significantly lowered compared to the use of pure 1,3-butadiene.

It is thus an object of the present invention to provide a process for hydrocyanating 1,3-butadiene over at least one catalyst, in which a 1,3-butadiene-containing reactant stream which can be obtained in an uncomplicated and inexpensive manner can be used.

The achievement of this object starts from a process for hydrocyanating 1,3-butadiene over at least one nickel(0) complex having phosphorus ligands as a catalyst. In the process according to the invention, the 1,3-butadiene is used in a mixture with n-butane.

According to the invention, it has been found that a mixture of 1,3-butadiene and n-butane can be used in the hydrocyanation to 3-pentenenitrile. This mixture may additionally comprise 2-butene.

The mixture used as a reactant for the process according to the invention contains preferably from 60 to 90% by volume, more preferably from 65 to 85% by volume, in particular from 70 to 80% by volume, of 1,3-butadiene, in each case based on 1,3-butadiene and n-butane. In addition, the mixture used in the process according to the invention contains preferably from 40 to 10% by volume, more preferably from 35 to 15% by volume, in particular from 30 to 20% by volume, of n-butane, in each case based on 1,3-butadiene and n-butane.

In a particularly preferred embodiment of the process according to the invention, the mixture which is used in the process according to the invention for hydrocyanation is obtained as the product of value stream e according to German patent application DE 103 61 822.8, having an earlier priority date but unpublished at the priority date of the present application, to BASF AG, which relates to a process for preparing 1,3-butadiene, by the following process steps:

A) providing a feed gas stream a comprising n-butane;

B) feeding the feed gas stream a comprising n-butane into at least one first dehydrogenation zone and nonoxidatively catalytically dehydrogenating n-butane to obtain a product gas stream b comprising n-butane, 1-butene, 2-butene, butadiene, hydrogen, low-boiling secondary constituents and in some cases steam;

C) feeding the product gas stream b of the nonoxidative catalytic dehydrogenation and an oxygenous gas into at least one second dehydrogenation zone and oxidatively dehydrogenating 1-butene and 2-butene to obtain a product gas stream c comprising n-butane, 2-butene, butadiene, hydrogen, low-boiling secondary constituents and steam, said product gas stream c having a higher content of butadiene than the product gas stream b;

D) removing steam, low-boiling secondary constituents and steam to obtain a $C_4$ product gas stream d substantially consisting of n-butane, 2-butene and butadiene;

E) feeding the $C_4$ product gas stream d into a distillation zone and removing a butadiene/n-butane mixture as a product of value stream e.

This process for preparing the product of value stream e features particularly effective utilization of the raw materials. Thus, losses of the n-butane raw material are minimized by recycling unconverted n-butane into the dehydrogenation. The coupling of nonoxidative catalytic dehydrogenation and oxidative dehydrogenation achieves a high butadiene yield.

In a first process part A, a feed gas stream a comprising n-butane is provided. Typically, the starting raw materials are n-butane-rich gas mixtures such as liquefied petroleum gas (LPG). LPG comprises substantially saturated $C_2$-$C_5$ hydrocarbons. In addition, it also contains methane and traces of $C_6^+$ hydrocarbons. The composition of LPG may vary markedly. Advantageously, the LPG used contains at least 10% by weight of butanes.

Alternatively, a refined $C_4$ stream from crackers or refineries may be used.

In one variant, the provision of the dehydrogenation feed gas stream comprising n-butane comprises the steps of (A1) providing a liquefied petroleum gas (LPG) stream, (A2) removing propane and any methane, ethane and $C_5^+$ hydrocarbons (mainly pentanes, additionally hexanes, heptanes, benzene, toluene) from the LPG stream to obtain a stream comprising butanes (n-butane and isobutane), (A3) removing isobutane from the stream containing butanes to obtain the feed gas stream comprising n-butane, and, if appropriate, isomerizing the isobutane removed to give an n-butane/isobutane mixture and recycling the n-butane/isobutane mixture into the isobutane removal.

Propane and any methane, ethane and $C_5^+$ hydrocarbons are removed, for example, in one or more customary rectification columns. For example, in a first column, low boilers (methane, ethane, propane) may be removed overhead and, in a second column, high boilers ($C_5^+$ hydrocarbons) may be removed at the bottom of the column. A stream comprising butanes (n-butane and isobutane) is obtained, from which isobutane is removed, for example in a customary rectification column. The remaining stream comprising n-butane is used as the feed gas stream for the downstream butane dehydrogenation.

The isobutane stream removed is preferably subjected to an isomerization. To this end, the stream comprising isobutane is fed into an isomerization reactor. The isomerization of isobutane to n-butane may be carried out as described in GB-A 2 018 815. An n-butane/isobutane mixture is obtained and is fed into the n-butane/isobutane separating column.

The isobutane stream removed may also be sent to a further use, for example for preparing methacrylic acid, polyisobutene or methyl tert-butyl ether.

In one process part B, the feed gas stream comprising n-butane is fed into a dehydrogenation zone and subjected to a nonoxidative catalytic dehydrogenation. In this dehydrogenation, n-butane is partly dehydrogenated in a dehydrogenation reactor over a dehydrogenating catalyst to give 1-butene and 2-butene, and butadiene is also formed. In addition, hydrogen and small amounts of methane, ethane, ethene, propane and propene are obtained. Depending on the method of the dehydrogenation, carbon oxides ($CO$, $CO_2$), water and nitrogen may also be present in the product gas mixture of the nonoxidative catalytic n-butane dehydrogenation. Unconverted n-butane is additionally present in the product gas mixture.

The nonoxidative catalytic n-butane dehydrogenation may be carried out with or without oxygenous gas as a cofeed.

One feature of the nonoxidative method (dehydrogenation with formation of free hydrogen) compared to an oxidative method is the presence of hydrogen in the effluent gas. In the oxidative dehydrogenation, free hydrogen is not formed in substantial amounts.

The nonoxidative catalytic n-butane dehydrogenation may in principle be carried out in any reactor types and methods disclosed by the prior art. A comparatively comprehensive description of dehydrogenation processes suitable in accordance with the invention is also contained in "Catalytica® Studies Division, Oxidative Dehydrogenation and Alternative Dehydrogenation Processes" (Study Number 4192 OD, 1993, 430 Ferguson Drive, Mountain View, Calif., 94043-5272, USA).

A suitable reactor form is the fixed bed tubular or tube bundle reactor. In these reactors, the catalyst (dehydrogenation catalyst and, when working with oxygen as the cofeed, if appropriate a specialized oxidation catalyst) is disposed as a fixed bed in a reaction tube or in a bundle of reaction tubes. The reaction tubes are customarily heated indirectly by the combustion of a gas, for example a hydrocarbon such as methane, in the space surrounding the reaction tubes. It is favorable to apply this indirect form of heating only to about the first 20 to 30% of the length of the fixed bed and to heat the remaining bed length to the required reaction temperature by the radiant heat released in the course of indirect heating. Customary reaction tube internal diameters are from about 10 to 15 cm. A typical dehydrogenation tube bundle reactor comprises from about 300 to 1000 reaction tubes. The internal temperature in the reaction tubes typically varies in the range from 300 to 1200° C., preferably in the range from 500 to 1000° C. The working pressure is customarily from 0.5 to 8 bar, frequently from 1 to 2 bar, when a small steam dilution is used (similar to the Linde process for propane dehydrogenation), or else from 3 to 8 bar when using a high steam dilution (similar to the steam active reforming process (STAR process) for dehydrogenating propane or butane of Phillips Petroleum Co., see U.S. Pat. No. 4,902,849, U.S. Pat. No. 4,996,387 and U.S. Pat. No. 5,389,342). Typical gas hourly space velocities (GHSV) are from 500 to 2000 $h^{-1}$, based on the hydrocarbon used. The catalyst geometry may, for example, be spherical or cylindrical (hollow or solid).

The nonoxidative catalytic n-butane dehydrogenation may also be carried out using the heterogeneous catalysis in a fluidized bed, as described in Chem. Eng. Sci. 1992 b, 47 (9-11) 2313. Appropriately, two fluidized beds are operated in parallel, of which one is generally in the process of regeneration. The working pressure is typically from 1 to 2 bar, the dehydrogenation temperature generally from 550 to 600° C. The heat required for the dehydrogenation is introduced into the reaction system by preheating the dehydrogenation catalyst to the reaction temperature. The admixing of an oxygenous cofeed allows the preheater to be dispensed with and the required heat to be generated directly in the reactor system by combustion of hydrogen and/or hydrocarbons in the presence of oxygen. If appropriate, a hydrogen-containing cofeed may additionally be admixed.

The nonoxidative catalytic n-butane dehydrogenation may be carried out in a tray reactor with or without oxygenous gas as a cofeed. This reactor comprises one or more successive catalyst beds. The number of catalyst beds may be from 1 to 20, advantageously from 1 to 6, preferably from 1 to 4 and in particular from 1 to 3. The catalyst beds are preferably flowed through radially or axially by the reaction gas. In general, such a tray reactor is operated using a fixed catalyst bed. In the simplest case, the fixed catalyst beds are disposed axially in a shaft furnace reactor or in the annular gaps of concentric cylindrical grids. A shaft furnace reactor corresponds to one tray. Carrying out the dehydrogenation in a single shaft furnace reactor corresponds to a preferred embodiment, in which it is possible to work with oxygenous cofeed. In a further preferred embodiment, the dehydrogenation is carried out in a tray reactor having 3 catalyst beds. In a method without oxygenous gas as cofeed, the reaction gas mixture is subjected to intermediate heating in the tray reactor on its way from one catalyst bed to the next catalyst bed, for example by passing it over heat exchanger plates heated by hot gases or by passing it through tubes heated by hot combustion gases.

In a preferred embodiment of the process according to the invention, the nonoxidative catalytic n-butane dehydrogenation is carried out autothermally. To this end, the reaction gas mixture of the n-butane dehydrogenation is additionally admixed with oxygen in at least one reaction zone and the hydrogen and/or hydrocarbon present in the reaction gas mixture is at least partly combusted, which directly generates in the reaction gas mixture at least a portion of the heat required for dehydrogenation in the at least one reaction zone.

In general, the amount of oxygenous gas added to the reaction gas mixture is selected in such a manner that the amount of heat required for the dehydrogenation of n-butane is generated by the combustion of the hydrogen present in the reaction gas mixture and any hydrocarbons present in the reaction gas mixture and/or carbon present in the form of coke. In general, the total amount of oxygen supplied, based on the total amount of butane, is from 0.001 to 0.5 mol/mol, preferably from 0.005 to 0.2 mol/mol, more preferably from 0.05 to 0.2 mol/mol. Oxygen may be used either as pure oxygen or as an oxygenous gas in the mixture with inert gases, for example in the form of air. The inert gases and the gases resulting from the combustion generally provide additional dilution and therefore promote the heterogeneously catalyzed dehydrogenation.

The hydrogen combusted to generate heat is the hydrogen formed in the catalytic n-butane dehydrogenation and also any hydrogen additionally added to the reaction gas mixture as hydrogenous gas. The amount of hydrogen present should preferably be such that the $H_2/O_2$ molar ratio in the reaction gas mixture immediately after the oxygen is fed in is from 1 to 10 mol/mol, preferably from 2 to 5 mol/mol. In multistage reactors, this applies to every intermediate feed of oxygenous and any hydrogenous gas.

The hydrogen is combusted catalytically. The dehydrogenation catalyst used generally also catalyzes the combustion of the hydrocarbons and of hydrogen with oxygen, so that in principle no specialized oxidation catalyst is required apart from it. In one embodiment, operation is effected in the presence of one or more oxidation catalysts which selectively catalyze the combustion of hydrogen to oxygen in the presence of hydrocarbons. The combustion of these hydrocarbons with oxygen to give CO, $CO_2$ and water therefore proceeds only to a minor extent. The dehydrogenation catalyst and the oxidation catalyst are preferably present in different reaction zones.

When the reaction is carried out in more than one stage, the oxidation catalyst may be present only in one, in more than one or in all reaction zones.

Preference is given to disposing the catalyst which selectively catalyzes the oxidation of hydrogen at the points where there are higher partial oxygen pressures than at other points in the reactor, in particular near the feed point for the oxygenous gas. The oxygenous gas and/or hydrogenous gas may be fed in at one or more points in the reactor.

In one embodiment, there is intermediate feeding of oxygenous gas and of hydrogenous gas upstream of each tray of a tray reactor. In a further embodiment of the process according to the invention, oxygenous gas and hydrogenous gas are fed in upstream of each tray except the first tray. In one embodiment, a layer of a specialized oxidation catalyst is present downstream of every feed point, followed by a layer of the dehydrogenation catalyst. In a further embodiment, no specialized oxidation catalyst is present. The dehydrogenation temperature is generally from 400 to 1100° C., the pressure in the last catalyst bed of the tray reactor is generally from 0.2 to 5 bar, preferably from 1 to 3 bar. The GHSV is generally from 500 to 2000 $h^{-1}$, and in high-load operation, even up to 100 000 $h^{-1}$, preferably from 4000 to 16 000 $h^{-1}$.

A preferred catalyst which selectively catalyzes the combustion of hydrogen comprises oxides and/or phosphates selected from the group consisting of the oxides and/or phosphates of germanium, tin, lead, arsenic, antimony and bismuth. A further preferred catalyst which catalyzes the combustion of hydrogen comprises a noble metal of transition group VIII and/or I of the periodic table.

The dehydrogenation catalysts used generally comprise a support and an active composition. The support generally consists of a heat-resistant oxide or mixed oxide. The dehydrogenation catalysts preferably comprise a metal oxide selected from the group consisting of zirconium dioxide, zinc oxide, aluminum oxide, silicon dioxide, titanium dioxide, magnesium oxide, lanthanum oxide, cerium oxide and mixtures thereof, as a support. The mixtures may be physical mixtures or else chemical mixed phases such as magnesium aluminum oxide or zinc aluminum oxide mixed oxides. Preferred supports are zirconium dioxide and/or silicon dioxide, and particular preference is given to mixtures of zirconium dioxide and silicon dioxide.

The active composition of the dehydrogenation catalysts generally comprises one or more elements of transition group VIII of the periodic table, preferably platinum and/or palladium, more preferably platinum. Furthermore, the dehydrogenation catalysts may comprise one or more elements of main group I and/or II of the periodic table, preferably potassium and/or cesium. The dehydrogenation catalysts may further comprise one or more elements of transition group III of the periodic table including the lanthanides and actinides, preferably lanthanum and/or cerium. Finally, the dehydrogenation catalysts may comprise one or more elements of main group III and/or IV of the periodic table, preferably one or more elements selected from the group consisting of boron, gallium, silicon, germanium, tin and lead, more preferably tin.

In a preferred embodiment, the dehydrogenation catalyst comprises at least one element of transition group VIII, at least one element of main group I and/or II, at least one element of main group III and/or IV and at least one element of transition group III including the lanthanides and actinides.

For example, all dehydrogenation catalysts which are disclosed by WO 99/46039, U.S. Pat. No. 4,788,371, EP-A 705 136, WO 99/29420, U.S. Pat. No. 5,220,091, U.S. Pat. No. 5,430,220, U.S. Pat. No. 5,877,369, EP 0 117 146, DE-A 199 37 106, DE-A 199 37 105 and DE-A 199 37 107 may be used according to the invention. Particularly preferred catalysts for the above-described variants of autothermal n-butane dehydrogenation are the catalysts according to examples 1, 2, 3 and 4 of DE-A 199 37 107.

Preference is given to carrying out the n-butane dehydrogenation in the presence of steam. The added steam serves as a heat carrier and supports the gasification of organic deposits on the catalysts, which counteracts carbonization of the catalysts and increases the onstream time of the catalysts. The organic deposits are converted to carbon monoxide, carbon dioxide and in some cases water.

The dehydrogenation catalyst may be regenerated in a manner known per se. For instance, steam may be added to the reaction gas mixture or an oxygenous gas may be passed from time to time over the catalyst bed at elevated temperature and the deposited carbon burnt off. Dilution with steam shifts the equilibrium toward the products of dehydrogenation. After the regeneration, the catalyst is reduced with a hydrogenous gas if appropriate.

The nonoxidative catalytic n-butane dehydrogenation provides a gas mixture which, in addition to butadiene, 1-butene, 2-butene and unconverted n-butane, comprises secondary constituents. Customary secondary constituents include hydrogen, steam, nitrogen, CO and $CO_2$, methane, ethane, ethene, propane and propene. The composition of the gas mixture leaving the first dehydrogenation zone may be highly variable depending on the dehydrogenation method. For instance, in the preferred autothermal dehydrogenation with feeding in of oxygen and additional hydrogen, the product gas mixture comprises a comparatively high content of steam and carbon oxides. In methods without feeding in of oxygen, the product gas mixture of the nonoxidative dehydrogenation has a comparatively high hydrogen content.

The product gas stream of the nonoxidative autothermal n-butane dehydrogenation typically contains from 0.1 to 15% by volume of butadiene, from 1 to 15% by volume of 1-butene, from 1 to 25% by volume of 2-butene (cis/trans-2-butene), from 20 to 70% by volume of n-butane, from 1 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen and from 0 to 5% by volume of carbon oxides.

The product gas stream b leaving the first dehydrogenation zone is preferably separated into two substreams, of which only one of the two substreams is subjected to the further process parts C to G and the second substream may be recycled into the first dehydrogenation zone. A corresponding procedure is described in DE-A 102 11 275. However, the entire product gas stream b of the nonoxidative catalytic n-butane dehydrogenation may also be subjected to the further process parts C to F.

According to the invention, the nonoxidative catalytic dehydrogenation is followed downstream by an oxidative dehydrogenation (oxydehydrogenation) as process part C. This substantially dehydrogenates 1-butene and 2-butene to 1,3-butadiene, and 1-butene is generally virtually fully depleted.

This may in principle be carried out in all reactor types and methods disclosed by the prior art, for example in a fluidized bed, in a tray furnace, in a fixed bed tubular or tube bundle reactor, or in a plate heat exchanger reactor. A plate heat exchanger reactor is described, for example, in DE-A 199 52 964. To carry out the oxidative dehydrogenation, a gas mixture is required which has a molar oxygen:n-butenes ratio of at least 0.5. Preference is given to working at an oxyen:n-butenes ratio of from 0.55 to 50. To attain this value, the product gas mixture stemming from the nonoxidative catalytic dehydrogenation is generally mixed with oxygen or an oxygenous gas, for example air. The resulting oxygenous gas mixture is then fed to the oxydehydrogenation.

The catalysts which are particularly suitable for the oxydehydrogenation are generally based on an Mo—Bi—O multimetal oxide system which generally additionally comprises iron. In general, the catalyst system also comprises additional components from groups 1 to 15 of the periodic table, for example potassium, magnesium, zirconium, chromium, nickel, cobalt, cadmium, tin, lead, germanium, lanthanum, manganese, tungsten, phosphorus, cerium, aluminum or silicon.

Suitable catalysts and their preparation are described, for example, in U.S. Pat. No. 4,423,281 ($Mo_{12}BiNi_8Pb_{0.5}Cr_3K_{0.2}O_x$ and $Mo_{12}Bi_bNi_7Al_3Cr_{0.5}K_{0.5}O_x$), U.S. Pat. No. 4,336,409 ($Mo_{12}BiNi_6Cd_2Cr_3P_{0.5}O_x$), DE-A 26 00 128 ($Mo_{12}BiNi_{0.5}Cr_3P_{0.5}Mg_{7.5}K_{0.1}O_x+SiO_2$) and DE-A 24 40 329 ($Mo_{12}BiCo_{4.5}Ni_{2.5}Cr_3P_{0.5}K_{0.1}O_x$).

The stoichiometry of the active composition of a multitude of multimetal oxide catalysts suitable for the oxydehydrogenation can be encompassed under the general formula (I)

$$Mo_{12}Bi_aFe_bCo_cNi_dCr_eX^1_fK_gO_x \qquad (I)$$

where the variables are defined as follows:
  $X^1$=W, Sn, Mn, La, Ce, Ge, Ti, Zr, Hf, Nb, P, Si, Sb, Al, Cd and/or Mg;
  a=from 0.5 to 5, preferably from 0.5 to 2;
  b=from 0 to 5, preferably from 2 to 4;
  c=from 0 to 10, preferably from 3 to 10;
  d=from 0 to 10;
  e=from 0 to 10, preferably from 0.1 to 4;
  f=from 0 to 5, preferably from 0.1 to 2;
  g=from 0 to 2, preferably from 0.01 to 1; and
  x=a number which is determined by the valency and frequency of the elements in (I) other than oxygen.

In the process according to the invention, preference is given to using an Mo—Bi—Fe—O multimetal oxide system for the oxydehydrogenation, and particular preference is given to an Mo—Bi—Fe—Cr—O or Mo—Bi—Fe—Zr—O multimetal oxide system. Preferred systems are described, for example, in U.S. Pat. No. 4,547,615 ($Mo_{12}BiFe_{0.1}Ni_8ZrCr_3K_{0.2}O_x$ and $Mo_{12}BiFe_{0.1}Ni_8AlCr_3K_{0.2}O_x$), U.S. Pat. No. 4,424,141 ($Mo_{12}BiFe_3CO_{4.5}Ni_{2.5}P_{0.5}K_{0.1}O_x+SiO_2$), DE-A 25 30 959 ($Mo_{12}BiFe_3CO_{4.5}Ni_{2.5}Cr_{0.5}K_{0.1}O_x$, $Mo_{13.75}BiFe_3CO_{4.5}Ni_{2.5}Ge_{0.5}K_{0.8}O_x$, $Mo_{12}BiFe_3CO_{4.5}Ni_{2.5}Mn_{0.5}K_{0.1}O_x$ and $Mo_{12}BiFe_3CO_{4.5}Ni_{2.5}La_{0.5}K_{0.1}O_x$), U.S. Pat. No. 3,911,039 ($Mo_{12}BiFe_3CO_{4.5}Ni_{2.5}Sn_{0.5}K_{0.1}O_x$), DE-A 25 30 959 and DE-A 24 47 825 ($Mo_{12}BiFe_3CO_{4.5}Ni_{2.5}W_{0.5}K_{0.1}O_x$). The preparation and characterization of the catalysts mentioned are described comprehensively in the documents cited.

The oxydehydrogenation catalyst is generally used as shaped bodies having an average size of over 2 mm. Owing to the pressure drop to be observed when performing the process, smaller shaped bodies are generally unsuitable. Examples of useful shaped bodies include tablets, cylinders, hollow cylinders, rings, spheres, strands, wagon wheels or extrudates. Special shapes, for example "trilobes" and "tristars" (see EP-A-0 593 646) or shaped bodies having at least one notch on the exterior (see U.S. Pat. No. 5,168,090) are likewise possible.

In general, the catalyst used may be used as an unsupported catalyst. In this case, the entire shaped catalyst body consists of the active composition, including any auxiliary, such as graphite or pore former and also further components. In particular, it has proven advantageous to use the Mo—Bi—Fe—O catalyst preferably used for the oxydehydrogenation of n-butenes to butadiene as an unsupported catalyst. Furthermore, it is possible to apply the active compositions of the catalysts to a support, for example an inorganic, oxidic shaped body. Such catalysts are generally referred to as coated catalysts.

The oxydehydrogenation is generally carried out at a temperature of from 220 to 490° C., preferably from 250 to 450° C. and more preferably from 300 to 350° C. A reactor entrance pressure is selected which is sufficient to overcome the flow resistances in the plant and the subsequent workup. This reactor entrance pressure is generally from 0.005 to 1 MPa above atmospheric pressure, preferably from 0.01 to 0.5 MPa above atmospheric pressure. By its nature, the gas pressure applied in the entrance region of the reactor substantially falls over the entire catalyst bed.

The coupling of the nonoxidative catalytic, preferably autothermal, dehydrogenation with the oxidative dehydrogenation of the n-butenes formed provides a very much higher yield of butadiene based on n-butane used. The nonoxidative dehydrogenation can also be operated in a gentler manner. Comparable butadiene yields would only be achievable with an exclusively nonoxidative dehydrogenation at the cost of distinctly reduced selectivities. An exclusively oxidative dehydrogenation would only achieve low n-butane conversions.

In addition to butadiene and unconverted n-butane, the product gas stream c leaving the oxidative dehydrogenation comprises 2-butene and steam. As secondary constituents it generally comprises carbon monoxide, carbon dioxide, oxygen, nitrogen, methane, ethane, ethene, propane and propene, with or without hydrogen and also oxygenous hydrocarbons, known as oxygenates. In general, it only comprises very small proportions of 1-butene.

In general, the product gas stream c leaving the oxidative dehydrogenation has from 1 to 40% by volume of butadiene, from 20 to 80% by volume of n-butane, from 0.5 to 40% by volume of 2-butene, from 0 to 5% by volume of 1-butene, from 0 to 70% by volume of steam, from 0 to 10% by volume of low-boiling hydrocarbons (methane, ethane, ethene, propane and propene), from 0.1 to 40% by volume of hydrogen, from 0 to 70% by volume of nitrogen, from 0 to 10% by volume of carbon oxides and from 0 to 10% by volume of oxygenates. Oxygenates may be, for example, furan, acetic acid, maleic anhydride, formic acid and butyraldehyde.

In one process part, D, low-boiling secondary constituents other than the $C_4$ hydrocarbons (n-butane, isobutane, 1-butene, cis-/trans-2-butene, isobutene, butadiene) are at least partly, but preferentially substantially completely, removed from the product gas stream of the n-butane dehydrogenation to obtain a $C_4$ product gas stream d.

In one embodiment of the process according to the invention, water is initially removed from the product gas stream c in process part D. Water may be removed, for example, by condensing out by cooling and/or compressing the product gas stream c, and may be carried out in one or more cooling and/or compression stages.

The low-boiling secondary constituents may be removed from the product gas stream by customary separation processes such as distillation, rectification, membrane processes, absorption or adsorption.

To remove the hydrogen present in the product gas stream c, the product gas mixture, if appropriate on completion of cooling, is passed through a membrane, generally configured as a tube, which is permeable only to molecular hydrogen, for example in an indirect heat exchanger. The thus removed molecular hydrogen may, if required, be used at least partly in the dehydrogenation or else sent to another utilization, for example for generating electrical energy in fuel cells.

The carbon dioxide present in the product gas stream c may be removed by $CO_2$ gas scrubbing. The carbon dioxide gas scrubbing may be preceded upstream by a separate combustion stage in which carbon monoxide is selectively oxidized to carbon dioxide.

In a preferred embodiment of the process according to the invention, the uncondensable or low-boiling gas constituents such as hydrogen, oxygen, carbon oxides, the low-boiling hydrocarbons (methane, ethane, ethene, propane, propene) and any nitrogen are removed by means of a high-boiling absorbent in an absorption/desorption cycle to obtain a $C_4$ product gas stream c which consists substantially of the $C_4$ hydrocarbons. In general, at least 80% by volume, preferably at least 90% by volume, more preferably at least 95% by volume, of the $C_4$ product gas stream c consists of the $C_4$ hydrocarbons. The stream d consists substantially of n-butane, 2-butene and butadiene.

To this end, in an absorption stage, the product gas stream c, after preceding water removal, is contacted with an inert absorbent and the $C_4$ hydrocarbons are absorbed in the inert absorbent to obtain absorbent laden with $C_4$ hydrocarbons and an offgas comprising the remaining gas constituents. In a desorption stage, the $C_4$ hydrocarbons are released again from the absorbent.

Inert absorbents used in the absorption stage are generally high-boiling nonpolar solvents in which the $C_4$ hydrocarbon mixture to be removed has a distinctly higher solubility than the remaining gas constituents to be removed. The absorption may be effected by simply passing the product gas stream c through the absorbent. However, it may also be effected in columns or in rotary absorbers. Operation may be effected in cocurrent, countercurrent or crosscurrent. Examples of suitable absorption columns include tray columns having bubble-cap, centrifugal and/or sieve trays, columns having structured packings, for example sheet metal packings having a specific surface area of from 100 to 1000 $m^2/m^3$ such as Mellapak® 250 Y, and randomly packed columns. However, useful absorption columns also include trickle and spray towers, graphite block absorbers, surface absorbers such as thick-film and thin-film absorbers and also rotary columns, plate scrubbers, cross-spray scrubbers and rotary scrubbers.

Suitable absorbents are comparatively nonpolar organic solvents, for example aliphatic $C_8$- to $C_{18}$-alkenes, or aromatic hydrocarbons such as the middle oil fractions from paraffin distillation, or ethers having bulky groups, or mixtures of these solvents, to each of which a polar solvent such as 1,2-dimethyl phthalate may be added. Further suitable absorbents include esters of benzoic acid and phthalic acid with straight-chain $C_1$-$C_8$-alkanols, such as n-butyl benzoate, methyl benzoate, ethyl benzoate, dimethyl phthalate, diethyl phthalate, and also heat carrier oils, such as biphenyl and diphenyl ether, their chlorine derivatives and also triarylalkenes. A useful absorbent is a mixture of biphenyl and diphenyl ether, preferably in the azeotropic composition, for example the commercially available Diphyl®. Frequently, this solvent mixture contains dimethyl phthalate in an amount of 0.1 to 25% by weight. Further suitable absorbents are octanes, nonanes, decanes, undecanes, dodecanes, tridecanes, tetradecanes, pentadecanes, hexadecanes, heptadecanes and octadecanes, or fractions obtained from refinery streams which have the linear alkanes mentioned as main components.

For desorption of the $C_4$ hydrocarbons, the laden absorbent is heated and/or decompressed to a lower pressure. Alternatively, desorption may also be effected by stripping or in a combination of decompression, heating and stripping in one or more process steps. The absorbent regenerated in the desorption stage is recycled into the absorption stage.

In one process variant, the desorption step is carried out by decompressing and/or heating the laden desorbent.

The removal D is generally not entirely complete, so that, depending on the type of removal, small amounts or even only traces of the further gas constituents, especially of the low-boiling hydrocarbons, may still be present in the $C_4$ product gas stream.

In one process part E, the $C_4$ product gas stream d is fed into a distillation zone and separated into a product of value stream e composed of a butadiene/butane azeotrope and a stream e2 which consists substantially of n-butane and 2-butene.

The distillation zone generally consists of a distillation column having generally from 30 to 80, preferably from 40 to 75, theoretical plates. Suitable are, for example, bubble-cap tray columns, columns having random packings or structured packings, or dividing wall columns. The reflux ratio is generally from 10 to 50. The distillation is generally carried out at a pressure of from 5 to 20 bar.

In the upper section of the column, preferably at the top of the column, a butadiene/n-butane mixture e is drawn off. The butadiene/n-butane mixture may have the composition of the azeotrope or have a lower butadiene content; the butadiene/n-butane mixture generally contains at least 60% by volume of butadiene.

The thus generated product of value stream e which comprises 1,3-butadiene and n-butane may be used in a hydrocyanation of 1,3-butadiene.

It is not necessarily obligatory that the 1,3-butadiene is stabilized.

The hydrocyanation catalyst used is preferably a homogeneous nickel(0) catalyst which is stabilized with phosphorus ligands.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

$$P(X^1R^1)(X^2R^2)(X^3R^3) \qquad (I).$$

In the context of the present invention, compound I is a single compound or a mixture of different compounds of the aforementioned formula.

According to the invention, $X^1, X^2, X^3$ each independently are oxygen or a single bond. When all of the $X^1, X^2$ and $X^3$ groups are single bonds, compound (I) is a phosphine of the formula P(R¹ R² R³) with the definitions of R¹, R² and R³ specified in this description.

When two of the X¹, X² and X³ groups are single bonds and one is oxygen, compound I is a phosphinite of the formula P(OR¹)(R²)(R³) or P(R¹)(OR²)(R³) or P(R¹)(R²)(OR³) with the definitions of R¹, R² and R³ specified below.

When one of the X¹, X² and X³ groups is a single bond and two are oxygen, compound I is a phosphonite of the formula P(OR¹)(OR²)(R³) or P(R¹)(OR²)(OR³) or P(OR¹)(R²)(OR³) with the definitions of R¹, R² and R³ specified in this description.

In a preferred embodiment, all X¹, X² and X³ groups should be oxygen, so that compound I is advantageously a phosphite of the formula P(OR¹)(OR²)(OR³) with the definitions of R¹, R² and R³ specified below.

According to the invention, R¹, R², R³ are each independently identical or different organic radicals. R¹, R² and R³ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The R¹, R² and R³ groups may be bonded together directly, i.e. not solely via the central phosphorus atom. Preference is given to the R¹, R² and R³ groups not being bonded together directly.

In a preferred embodiment, R¹, R² and R³ groups are radicals selected from the group consisting of phenyl, o-tolyl, m-tolyl and p-tolyl. In a particularly preferred embodiment, a maximum of two of the R¹, R² and R³ groups should be phenyl groups.

In another preferred embodiment, a maximum of two of the R¹, R² and R³ groups should be o-tolyl groups.

Particularly preferred compounds I which may be used are those of the formula I a $$(o\text{-tolyl-O-})_w(m\text{-tolyl-O-})_x(p\text{-tolyl-O-})_y(\text{phenyl-O}—)_zP \qquad (I\ a)$$

where w, x, y, z are each a natural number, and the following conditions apply: w+x+y+z=3 and w, z≦2, Such compounds Ia are, for example, (p-tolyl-O-)(phenyl-O—)₂P, (m-tolyl-O-)(phenyl-O—)₂P, (o-tolyl-O-)(phenyl-O—)₂P, (p-tolyl-O-)₂(phenyl-O—)P, (m-tolyl-O-)₂(phenyl-O—)P, (o-tolyl-O-)₂(phenyl-O—)P, (m-tolyl-O-)(p-tolyl-O-)(phenyl-O—)P, (o-tolyl-O-)(p-tolyl-O-)(phenyl-O—)P, (o-tolyl-O-)(m-tolyl-O-)(phenyl-O—)P, (p-tolyl-O—)₃P, (m-tolyl-O-)(p-tolyl-O—)₂P, (o-tolyl-O-)(p-tolyl-O—)₂P, (m-tolyl-O-)₂(p-tolyl-O—)P, (o-tolyl-O-)₂(p-tolyl-O—)P, (o-tolyl-O-)(m-tolyl-O-)(p-tolyl-O—)P, (m-tolyl-O—)₃P, (o-tolyl-O-)(m-tolyl-O—)₂P, (O-tolyl-O-)₂(m-tolyl-O—)P or mixtures of such compounds.

Mixtures comprising (m-tolyl-O—)₃P, (m-tolyl-O-)₂(p-tolyl-O—)P, (m-tolyl-O-)(p-tolyl-O—)₂P and (p-tolyl-O—)₃P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

$$P(O—R^1)_x(O—R^2)_y(O—R^3)_z(O—R^4)_p \qquad (I\ b)$$

where
R¹: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, R²: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, R³: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, R⁴: aromatic radical which bears substituents other than those defined for R¹, R² and R³ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2,
y, z, p: each independently 0, 1 or 2, with the proviso that x+y+z+p=3.

Preferred phosphites of the formula I b can be taken from DE-A 199 53 058. The R¹ radical may advantageously be o-tolyl, o-ethylphenyl, o-n-propylphenyl, o-isopropylphenyl, o-n-butylphenyl, o-sec-butylphenyl, o-tert-butylphenyl, (o-phenyl)phenyl or 1-naphthyl groups.

Preferred R² radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous R³ radicals are p-tolyl, p-ethylphenyl, p-n-propylphenyl, p-isopropylphenyl, p-n-butylphenyl, p-sec-butylphenyl, p-tert-butylphenyl or (p-phenyl)phenyl groups.

The R⁴ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and R¹, R² and R³ are each independently selected from o-isopropylphenyl, m-tolyl and p-tolyl, and R⁴ is phenyl.

Particularly preferred phosphites of the formula I b are those in which R¹ is the o-isopropylphenyl radical, R² is the m-tolyl radical and R³ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

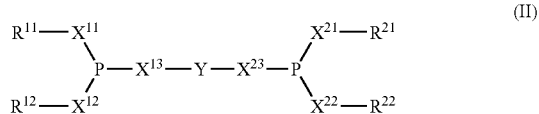

where $X^{11}, X^{12}, X^{13} X^{21}, X^{22}, X^{23}$ are each independently oxygen or a single bond $R^{11}, R^{12}$ are each independently identical or different, separate or bridged organic radicals $R^{21}, R^{22}$ are each independently identical or different, separate or bridged organic radicals, Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine.

The bridging group Y is preferably an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, and 21. In a particularly preferred embodiment, useful compounds are those specified in WO 01/14392, preferably the compounds illustrated there in formula V, VI, VII, VII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003 which has an earlier priority date but had not been published at the priority date of the present application.

The compounds I, I a, I b and II described and their preparation are known per se. The phosphorus ligands used may also be a mixture comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b $$P(O-R^1)_x(O-R^2)_y(O-R^3)_z(O-R^4)_p \qquad (Ib)$$

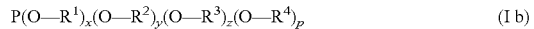

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

The hydrocyanation may be carried out in any suitable apparatus known to those skilled in the art. Useful apparatus for the reaction is customary apparatus, as described, for example, in: Kirk-Othmer, Encyclopedia of Chemical Technology, 4th Ed., Vol. 20, John Wiley & Sons, New York, 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, advantageous reactors have been found to be those having backmixing characteristics or batteries of reactors having backmixing characteristics. Particularly advantageous batteries of reactors having backmixing characteristics have been found to be those which are operated in crossflow mode in relation to the metering of hydrogen cyanide.

The hydrocyanation may be carried out in the presence or in the absence of a solvent. When a solvent is used, the solvent should be liquid and inert toward the unsaturated compounds and the at least one catalyst at the given reaction temperature and the given reaction pressure. In general, the solvents used are hydrocarbons, for example benzene or xylene, or nitriles, for example acetonitrile or benzonitrile. However, preference is given to using a ligand as the solvent.

The reaction may be carried out in batch mode, continuously or in semibatchwise operation.

The hydrocyanation may be carried out by charging the apparatus with all reactants. However, it is preferred when the apparatus is filled with the catalyst, the unsaturated organic compound and, if appropriate, the solvent. The gaseous hydrogen cyanide preferably floats over the surface of the reaction mixture or is passed through the reaction mixture. A further procedure for charging the apparatus is the filling of the apparatus with the catalyst, hydrogen cyanide and, if appropriate, the solvent, and slowly metering in the unsaturated compound to the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before the heating to reaction temperature. The reaction is carried out under conventional hydrocyanation conditions for temperature, atmosphere, reaction time, etc.

Preference is given to carrying out the hydrocyanation continuously in one or more stirred process steps. When a plurality of process steps is used, it is preferred that the process steps are connected in series. The product is transferred from one process step directly into the next process step. The hydrogen cyanide may be added directly in the first process step or between the individual process steps.

When the hydrocyanation is carried out in semibatchwise operation, it is preferred that the reactor is initially charged with the catalyst components and 1,3-butadiene, while hydrogen cyanide is metered into the reaction mixture over the reaction time.

The hydrocyanation is preferably carried out at absolute pressures of from 0.1 to 500 MPa, more preferably from 0.5 to 50 MPa, in particular from 1 to 5 MPa. The reaction is preferably carried out at temperatures of from 273 to 473 K, more preferably from 313 to 423 K, in particular from 333 to 393 K. Advantageous average mean residence times of the liquid reactor phase have been found to be in the range from 0.001 to 100 hours, preferably from 0.05 to 20 hours, more preferably from 0.1 to 5 hours, in each case per reactor.

In one embodiment, the hydrocyanation may be performed in the liquid phase in the presence of a gas phase and, if appropriate, of a solid suspended phase. In this case, the hydrogen cyanide and 1,3-butadiene starting materials may each be metered in liquid or gaseous form.

In a further embodiment, the hydrocyanation may be carried out in the liquid phase, in which case the pressure in the reactor is such that all feedstocks such as 1,3-butadiene, hydrogen cyanide and the at least one catalyst are metered in liquid form and are present in the liquid phase in the reaction mixture. A solid suspended phase may be present in the reaction mixture and may also be metered in together with the at least one catalyst, for example consisting of degradation products of the catalyst, comprising nickel(II) compounds inter alia.

The product of value stream e which is used as the reactant stream which is used in the inventive in a preferred embodiment illustrated above comprises n-butane. After the hydrocyanation of 1,3-butadiene, this n-butane may be removed from the hydrocyanatin effluent and, for example, recycled into the generation of the product of value stream e.

In the hydrocyanation, unconverted n-butane is obtained in some cases and is recycled into the dehydrogenation to obtain 1,3-butadiene.

The process according to the invention is associated with a series of advantages. For instance, the use of a mixture of 1,3-butadiene and n-butane from the butane dehydrogenation leads to a reduction in costs compared to the use of pure 1,3-butadiene. In addition, the n-butane which is present in the hydrocyanation effluent may be recycled into the dehydrogenation to obtain 1,3-butadiene. There is no need to stabilize the 1,3-butadiene present in the mixture. This also replaces the unavoidable transport, which is demanding from a safety point of view, of the 1,3-butadiene to the apparatus for hydrocyanating 1,3-butadienes with an unproblematic transport of n-butane.

The present invention is illustrated in detail with reference to some working examples.

EXAMPLES

All experiments are carried out in a protective gas atmosphere.

The following abbreviations are used:
BD: 1,3-butadiene
THF: tetrahydrofuran

Hydrocyanation of BD/n-butane (90% by volume/10% by volume) to 2-methyl-3-butenenitrile/3-pentenenitrile

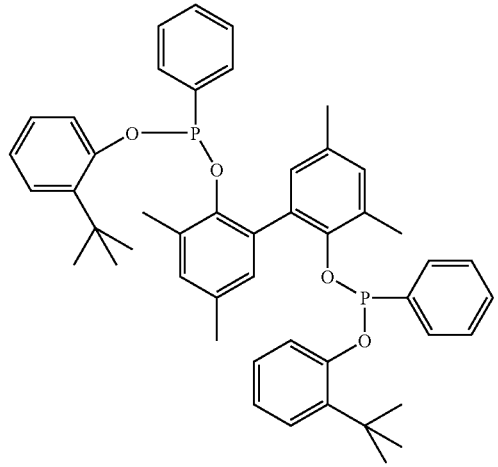

Ligand 1

Example 1

0.44 mmol of Ni(0)

1 eq. of Ni(COD)$_2$ is stirred with 3 eq. of ligand 1 in THF for 20 min. This solution is admixed with 727 eq. of BD which are used in the form of a BD/n-butane mixture having 90% by volume of BD and 10% by volume of n-butane, transferred to a glass autoclave at 25° C. and heated to 90° C. Over 60 min, 465 eq. of hydrogen cyanide in THF are now metered in and the mixture is stirred at 90° C. for a further 50 min. After 110 min, the 2-methyl-3-butenenitrile/3-pentenenitrile ratio is determined by gas chromatography (GC area percent). The 2-methyl-3-butenenitrile/3-pentenenitrile ratio is 1.7/1. The hydrogen cyanide conversion is >98% (Vollhard titration).

Hydrocyanation of BD/n-butane (80% by volume/20% by volume) to 2-methyl-3-butenenitrile/3-pentenenitrile Example 2

0.46 mmol of Ni(0)

1 eq. of Ni(COD)$_2$ is stirred with 3 eq. of ligand 1 in THF for 20 min. This solution is admixed with 727 eq. of BD which are used in the form of a BD/n-butane mixture having 80% by volume of BD and 20% by volume of n-butane, transferred to a glass autoclave at 25° C. and heated to 90° C. Over 60 min, 465 eq. of hydrogen cyanide in THF are now metered in and the mixture is stirred at 90° C. for a further 75 min. After 135 min, the 2-methyl-3-butenenitrile/3-pentenenitrile ratio is determined by gas chromatography (GC area percent). The 2-methyl-3-butenenitrile/3-pentenenitrile ratio is 1.4/1. The hydrogen cyanide conversion is >98% (Vollhard titration).

The examples are carried out with the exclusion of moisture under a protective gas atmosphere, for example composed of argon.

What is claimed is:

1. A process for hydrocyanating 1,3-butadiene over at least one nickel(0) catalyst having phosphorus ligands, the process comprising providing a mixture of from 60 to 90% by volume of 1,3-butadiene and from 40 to 10% by volume of n-butane, the mixture prepared by the following process steps:

A) providing a feed gas stream comprising the n-butane;
B) feeding the feed gas stream comprising n-butane into at least one first dehydrogenation zone and nonoxidatively catalytically dehydrogenating the n-butane to obtain a first product gas stream comprising n-butane, 1-butene, 2-butene, 1,3-butadiene, low-boiling secondary constituents and in some cases steam;
C) feeding the product gas stream of the nonoxidative catalytic dehydrogenation and an oxygenous gas into at least one second dehydrogenation zone and oxidatively dehydrogenating the 1-butene and the 2-butene to obtain a second product gas stream comprising n-butane, 2-butene, 1,3-butadiene, hydrogen, low-boiling secondary constituents and steam, said second product gas stream having a higher content of 1,3-butadiene than the first product gas stream;
D) removing the low-boiling secondary constituents and the steam to obtain a $C_4$ product gas stream substantially consisting of n-butane, 2-butene and 1,3-butadiene;
E) feeding the $C_4$ product gas stream into a distillation zone and removing a 1,3-butadiene/n-butane mixture.

2. The process according to claim 1, wherein the nonoxidative catalytic dehydrogenation of n-butane is carried out autothermally.

3. The process according to claim 1, wherein the feed gas stream comprising n-butane is obtained from liquefied petroleum gas (LPG).

4. The process according to claim 1, wherein the nickel(0) catalyst comprises phosphorus ligands which are selected from the group consisting of mono- or bidentate phosphines, phosphites, phosphinites, phosphonites and phosphinite phosphonites.

5. The process according to claim 2, wherein the feed gas stream comprising n-butane is obtained from liquefied petroleum gas (LPG).

* * * * *